(12) United States Patent
Poruthoor et al.

(10) Patent No.: US 8,987,544 B2
(45) Date of Patent: Mar. 24, 2015

(54) ARTICLE WITH HEAT-ACTIVATABLE EXPANDABLE STRUCTURES

(75) Inventors: Simon Poruthoor, Alpharetta, GA (US); Rebecca Griffin, Woodstock, GA (US); Lei Huang, Duluth, GA (US); Balaji K. Kandadai, Cumming, GA (US); Suzanne Murray, Appleton, WI (US); Hue Scott Snowden, Canton, GA (US); Herb Velazquez, Neenah, WI (US); Dean M. Wydeven, Appleton, WI (US); Ali Yahiaoui, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 635 days.

(21) Appl. No.: 12/971,741

(22) Filed: Dec. 17, 2010

(65) Prior Publication Data

US 2012/0157952 A1  Jun. 21, 2012

(51) Int. Cl.
| | |
|---|---|
| *A61F 13/494* | (2006.01) |
| *A61L 15/42* | (2006.01) |
| *A61F 13/472* | (2006.01) |
| *A61F 13/475* | (2006.01) |
| *A61F 13/00* | (2006.01) |

(52) U.S. Cl.
CPC ............ *A61L 15/42* (2013.01); *A61F 13/47263* (2013.01); *A61F 13/475* (2013.01); *A61F 13/00059* (2013.01)
USPC ........................................................ 604/369

(58) Field of Classification Search
USPC ............. 604/368, 385.21, 369; 428/106, 128; 101/368, 424; 523/201; 521/76
See application file for complete search history.

(56) References Cited

U.S. PATENT DOCUMENTS

| | | | |
|---|---|---|---|
| 3,854,978 | A | 12/1974 | Campbell, Sr. et al. |
| 3,930,090 | A | 12/1975 | Campbell, Sr. et al. |
| 4,200,103 | A | 4/1980 | Black et al. |
| 4,285,746 | A | 8/1981 | Depuy et al. |
| 4,526,825 | A | 7/1985 | Whitehead |
| 4,834,739 | A | 5/1989 | Linker, III et al. |

(Continued)

FOREIGN PATENT DOCUMENTS

| | | |
|---|---|---|
| CN | 201064524 Y | 5/2008 |
| EP | 0 941 727 A1 | 9/1999 |

(Continued)

OTHER PUBLICATIONS

Wilflex® Nupuff Base 10250NPF product sheet, Wilflex Plastisol Screen Printing Inks, PolyOne Corporation, Mar. 22, 2001, 1 page.

*Primary Examiner* — Tan-Uyen T Ho
*Assistant Examiner* — Peter S Vasat
(74) *Attorney, Agent, or Firm* — Kimberly-Clark Worldwide, Inc.

(57) ABSTRACT

An absorbent article has a longitudinal direction, a transverse direction, a first major surface which forms a body-facing surface of the absorbent article, and a second major surface disposed distally from the first major surface which forms a garment-facing surface of the absorbent article. The article includes an absorbent core positioned between the first major surface and the second major surface. The article also includes at least one heat-activatable expandable structure. The at least one heat-activatable expandable structure is disposed on or below the first major surface. Application of heat to the heat-activatable expandable structure causes the heat-activatable expandable barrier structure to form distinctive designs, barriers and/or channels.

19 Claims, 9 Drawing Sheets

(56) References Cited

U.S. PATENT DOCUMENTS

| | | | |
|---|---|---|---|
| 4,845,778 A | 7/1989 | Peterson | |
| 4,850,991 A * | 7/1989 | Nakanishi et al. | 604/387 |
| 5,338,766 A * | 8/1994 | Phan et al. | 521/63 |
| 5,578,025 A * | 11/1996 | May | 604/385.31 |
| 5,624,423 A | 4/1997 | Anjur et al. | |
| 5,653,166 A | 8/1997 | Mohammed et al. | |
| 5,795,921 A * | 8/1998 | Dyer et al. | 521/146 |
| 5,807,367 A * | 9/1998 | Dilnik et al. | 604/369 |
| 6,015,454 A | 1/2000 | Lacroix et al. | |
| 6,040,494 A * | 3/2000 | Kalentun et al. | 604/369 |
| 6,140,551 A | 10/2000 | Niemeyer et al. | |
| 6,297,424 B1 | 10/2001 | Olson et al. | |
| 6,416,502 B1 | 7/2002 | Connelly et al. | |
| 6,558,499 B1 | 5/2003 | Pargass et al. | |
| 6,569,136 B1 | 5/2003 | Tao et al. | |
| 6,592,562 B2 | 7/2003 | Menard et al. | |
| 6,626,879 B1 | 9/2003 | Ashton et al. | |
| 6,645,330 B2 | 11/2003 | Pargass et al. | |
| 6,737,114 B2 * | 5/2004 | Dawson et al. | 427/282 |
| 6,827,806 B2 | 12/2004 | Uitenbroek et al. | |
| 6,840,614 B2 | 1/2005 | Wagner et al. | |
| 6,936,648 B2 | 8/2005 | Bagwell et al. | |
| 6,958,430 B1 | 10/2005 | Marinelli | |
| 7,247,674 B2 | 7/2007 | Kitano et al. | |
| 8,216,200 B2 | 7/2012 | Meetz et al. | |
| 2003/0120237 A1 | 6/2003 | Guidotti | |
| 2004/0172772 A1 | 9/2004 | Santiago | |
| 2005/0152624 A1 | 7/2005 | Versluys | |
| 2005/0182194 A1 | 8/2005 | He et al. | |
| 2005/0257881 A1 | 11/2005 | Coose et al. | |
| 2006/0018953 A1 | 1/2006 | Guillon et al. | |
| 2006/0135925 A1 | 6/2006 | Hurley et al. | |
| 2007/0049884 A1 | 3/2007 | Long et al. | |
| 2007/0098962 A1 | 5/2007 | Laprade | |
| 2008/0145532 A1 | 6/2008 | McDonald | |
| 2008/0208151 A1 | 8/2008 | Zacharias et al. | |
| 2009/0192482 A1 | 7/2009 | Dodge, II et al. | |
| 2009/0271914 A1 | 11/2009 | Bauer | |
| 2009/0294045 A1 | 12/2009 | Marino et al. | |
| 2009/0326409 A1 | 12/2009 | Cohen et al. | |
| 2010/0000897 A1 | 1/2010 | Bumpass et al. | |
| 2010/0173119 A1 | 7/2010 | Vitarana et al. | |
| 2010/0179500 A1 | 7/2010 | Roe et al. | |
| 2010/0209521 A1 | 8/2010 | Schalkhammer | |
| 2010/0274213 A1 | 10/2010 | Gustin Bergstrom et al. | |
| 2011/0213325 A1 | 9/2011 | Gabrielii et al. | |
| 2012/0141698 A1 | 6/2012 | O'Leary et al. | |
| 2012/0157949 A1 * | 6/2012 | Knight et al. | 604/361 |

FOREIGN PATENT DOCUMENTS

| | | |
|---|---|---|
| EP | 1 917 940 A2 | 5/2008 |
| EP | 2250982 A1 | 11/2010 |
| KR | 10-2005-0085441 A | 8/2005 |
| KR | 10-2008-0011172 A | 1/2008 |
| WO | WO 98/13003 A1 | 4/1998 |
| WO | WO 01/00117 A2 | 1/2001 |
| WO | WO 2006/071211 A1 | 7/2006 |
| WO | WO 2007/024327 A1 | 3/2007 |
| WO | WO 2010/070503 A2 | 6/2010 |
| WO | WO 2010/072388 A2 | 7/2010 |
| WO | WO 2010/076679 A2 | 7/2010 |
| WO | WO 2012/082027 A1 | 6/2012 |

\* cited by examiner

ARTICLE WITH HEAT-ACTIVATABLE EXPANDABLE STRUCTURES

BACKGROUND

Absorbent articles such as feminine care products, incontinence products, and training pants are useful to absorb and contain body wastes. These products have developed to the extent that body exudates are quickly absorbed and retained away from the wearer's skin so that the wearer remains relatively dry and comfortable. Although the products enhance wearer dryness and comfort, the products can still be subject to leakage, particularly during a fluid insult gush, or when the article is becoming full. In one example, adult care wearers, especially women, are very concerned about leakage in public. Some wearers may be so bothered by leakage that if it occurs in a public place, they will avoid that place and situation for the rest of their life. Leakage is therefore a very undesirable characteristic in an adult care product.

Similarly, leakage from catamenial products poses a major problem to women and can be a social embarrassment, especially if it happens in public places. Current products exist that can delay or minimize leakage through length extension, material use, etc. There exist, however, situations in which women unexpectedly experience a gush of fluid, or unknowingly wear catamenial products beyond leakage points and risk staining their clothes. A woman might also make several trips to the bathroom to check her pad for fear of leakage. Such behavior can make menstruation a more inconvenient experience than it needs to be.

In an attempt to reduce or eliminate the occurrence of leakage, it may be desirable to maintain absorbent articles in close contact with the wearer's body. Such close body fit can allow the absorbent article to absorb body exudates at their source. Achieving close body fit limits the chance for the body exudates to flow off of or out of the absorbent article. However, good body contact may not always be available, particularly along the side regions of an article, which can lead to leakage. In attempts to address this issue, leakage protection features have been included in articles. In general, such leakage protection features are typically 3-dimensional barrier structures for good body fit and to capture any excess fluid which fails to be absorbed into the pad. However, these barriers tend to add bulk and non-uniformity to the product, making the product more difficult to manufacture and package. Thus, there is a need for an absorbent article which provides close body fit and/or better leak protection, particularly after a fluid insult, while reducing manufacturing and/or packaging difficulties.

SUMMARY

In response to the needs discussed above, a new absorbent article has been developed, which will allow women to maintain their active lifestyle with confidence, even on heavy-flow days. The heat-activatable expandable structures present in the invention have the ability to stay flat before activation, hence providing ease of manufacture, ease of packaging, and discrete storage. Upon activation, the heat-activatable expandable structures activate and expand to the desired shape, creating embossments, barriers, channels, and/or visual patterns on or between various layers of the absorbent article, thus allowing improved control of fluid to flow on or between the layers as well as improved visual appearance.

In some aspects, the absorbent article has a longitudinal direction, a transverse direction, a longitudinally-extending centerline, a transverse-extending centerline, first and second longitudinally opposed end portions, and first and second side edges. The absorbent article includes a first major surface which forms a body-facing surface of the absorbent article; a second major surface disposed distally from the first major surface which forms a garment-facing surface of the absorbent article; an absorbent core positioned between the first major surface and the second major surface; at least one heat-activatable expandable structure having an inward-facing side and an outward-facing side. The at least one heat-activatable expandable structure is disposed on or between the first major surface and the absorbent core.

In some aspects, the at least one expandable structure may include a an expandable ink.

In some aspects, the absorbent article comprises a heat activatable expandable structure on the first major surface, the heat activatable expandable structure extending around the periphery of the first major surface. In some aspects, the at least one heat-activatable expandable structure is positioned around a target zone of the absorbent article.

In some aspects, the absorbent article further comprises side panels for attaching the absorbent article to an undergarment. In other aspects, the absorbent article further comprises a garment fastening system for attaching the absorbent article to an undergarment.

In some aspects, the absorbent article further comprises at least one of an intake layer, a cover, and/or a backsheet. In other aspects, the absorbent article is a feminine care pad.

In a further embodiment, a method of preparing an absorbent article includes the steps of:

1) providing an absorbent article having a longitudinal direction, a transverse direction, a longitudinally-extending centerline, a transverse-extending centerline, first and second longitudinally opposed end portions, and first and second side edges, the absorbent article including components including:
   a first major surface which forms a body-facing surface of the absorbent article;
   a second major surface disposed distally from the first major surface which forms a garment-facing surface of the absorbent article; and
   an absorbent core positioned between the first major surface and the second major surface;

2) applying at least one heat-activatable expandable structure onto a component of the absorbent article; and 3) heating the at least one heat-activatable expandable structure to expand the volume of the at least one heat-activatable expandable structure.

In some aspects, the applying step further includes printing at least one heat activatable expandable structure onto the first major surface. In further aspects, the applying step further includes printing at least one heat activatable expandable structure onto the absorbent core. In even further aspects, the heat-activatable expandable structure may be applied below the first major surface.

In some aspects, the at least one heat-activatable expandable structure is heated to a temperature greater than about 100 degrees Fahrenheit. In further aspects, the at least one heat-activatable expandable structure is heated to a temperature greater than about 100 degrees Fahrenheit for a period of time greater than about 0.5 seconds.

In some aspects, the at least one heat-activatable expandable structure expands during the heating step by about 100 percent in volume.

In some aspects, the at least one heat-activatable expandable structure increases in thickness by greater than about 0.1 millimeter during the heating step.

In some aspects, the at least one heat-activatable expandable structure comprises a heat-activatable expandable ink.

Numerous other features and advantages of the present invention will appear from the following description. In the description, reference is made to exemplary embodiments of the invention. Such embodiments do not represent the full scope of the invention. Reference should therefore be made to the claims herein for interpreting the full scope of the invention. In the interest of brevity and conciseness, any ranges of values set forth in this specification contemplate all values within the range and are to be construed as support for claims reciting any sub-ranges having endpoints which are real number values within the specified range in question. By way of a hypothetical illustrative example, a disclosure in this specification of a range of from 1 to 5 shall be considered to support claims to any of the following ranges: 1-5; 1-4; 1-3; 1-2; 2-5; 2-4; 2-3; 3-5; 3-4; and 4-5, as well as fractions thereof.

FIGURES

The foregoing and other features, aspects and advantages of the present invention will become better understood with regard to the following description, appended claims and accompanying drawings where:

Figure 1:
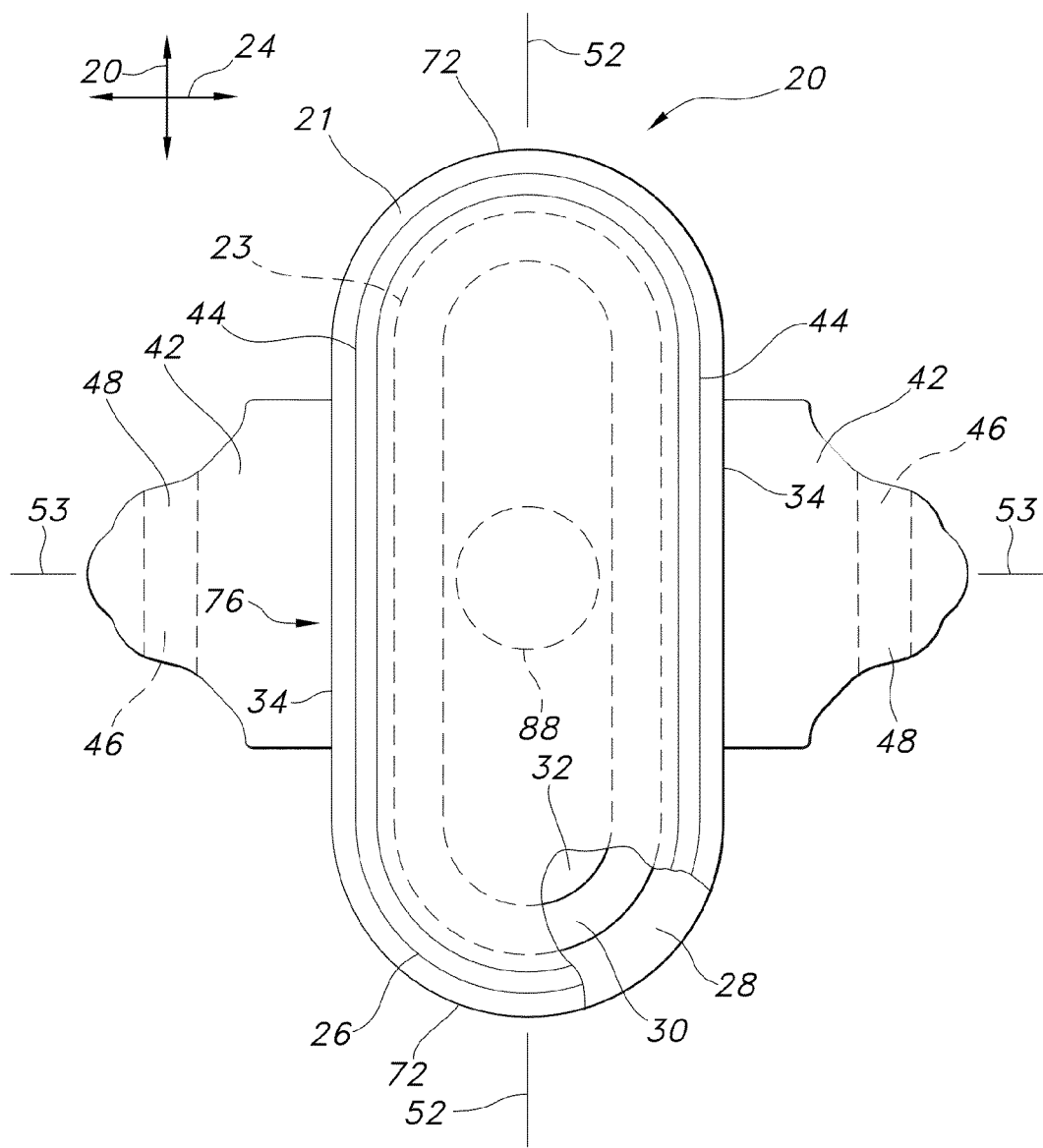
FIG. 1 is a top view of one embodiment of the absorbent article of the present invention.

Repeated use of reference characters in the present specification and drawings is intended to represent the same or analogous features or elements of the present invention.

DEFINITIONS

It should be noted that, when employed in the present disclosure, the terms "comprises," "comprising" and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

The term "absorbent article" generally refers to devices which can absorb and contain fluids. For example, personal care absorbent articles refer to devices which are placed against or near the skin to absorb and contain the various fluids discharged from the body.

The term "attach" and its derivatives refer to the joining, adhering, connecting, bonding, sewing together, or the like, of two elements. Two elements will be considered to be attached together when they are integral with one another or attached directly to one another or indirectly to one another, such as when each is directly attached to intermediate elements. "Attach" and its derivatives include permanent, releasable, or refastenable attachment. In addition, the attachment can be completed either during the manufacturing process or by the end wearer.

The term "bond" and its derivatives refer to the joining, adhering, connecting, attaching, sewing together, or the like, of two elements. Two elements will be considered to be bonded together when they are bonded directly to one another or indirectly to one another, such as when each is directly bonded to intermediate elements. "Bond" and its derivatives include permanent, releasable, or refastenable bonding.

The term "coform" refers to a blend of meltblown fibers and absorbent fibers such as cellulosic fibers that can be formed by air forming a meltblown polymer material while simultaneously blowing air-suspended fibers into the stream of meltblown fibers. The coform material may also include other materials, such as superabsorbent materials. The meltblown fibers and absorbent fibers are collected on a forming surface, such as provided by a foraminous belt. The forming surface may include a gas-pervious material that has been placed onto the forming surface.

The term "complex liquid" describes a liquid generally characterized as being a viscoelastic liquid comprising multiple components having inhomogeneous physical and/or chemical properties. It is the inhomogeneous properties of the multiple components that challenge the efficacy of an absorbent or adsorbent material in the handling of complex liquids. In contrast with complex liquids, simple liquids, such as, for example, urine, physiological saline, water and the like, are generally characterized as being relatively low-viscosity and comprising one or more components having homogeneous physical and/or chemical properties. As a result of having homogeneous properties, the one or more components of simple liquids behave substantially similarly during absorption or adsorption, although some components of the simple liquids may be absorbed or adsorbed more readily than others. Although a complex liquid is generally characterized herein as including specific components having inhomogeneous properties, each specific component of a complex liquid generally has homogeneous properties. Consider, for example, a representative complex body-liquid having three specific components: red blood cells, blood protein molecules and water molecules. Upon examination, one skilled in the art could easily distinguish between each of the three specific components according to their generally inhomogeneous properties. Moreover, when examining a particular specific component such as the red blood cell component, one skilled in the art could easily recognize the generally homogeneous properties of the red blood cells.

The term "connect" and its derivatives refer to the joining, adhering, bonding, attaching, sewing together, or the like, of two elements. Two elements will be considered to be connected together when they are connected directly to one another or indirectly to one another, such as when each is directly connected to intermediate elements. "Connect" and its derivatives include permanent, releasable, or refastenable connection. In addition, the connecting can be completed either during the manufacturing process or by the end wearer.

The term "disposable" is used herein to describe absorbent articles that are not intended to be laundered or otherwise restored or reused as an absorbent article after a single use.

The terms "disposed on," "disposed along," "disposed with," or "disposed toward" and variations thereof are intended to mean that one element can be integral with another element, or that one element can be a separate structure bonded to or placed with or placed near another element.

The terms "elastic," "elasticized," "elasticity," and "elastomeric" mean that property of a material or composite by virtue of which it tends to recover its original size and shape after removal of a force causing a deformation. Suitably, an elastic material or composite can be elongated by at least 50 percent (to 150 percent) of its relaxed length and will recover, upon release of the applied force, at least 40 percent of its elongation.

The term "fiber" refers to a continuous or discontinuous member having a high ratio of length to diameter or width. Thus, a fiber may be a filament, a thread, a strand, a yarn, or any other member or combination of these members.

The term "hydrophilic" describes materials which are wetted by aqueous liquids in contact with the materials. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, materials having contact angles less than 90 degrees are designated "wettable" or "hydrophilic," and fibers having contact angles greater than 90 degrees are designated "nonwettable" or "hydrophobic".

The term "join" and its derivatives refer to the connecting, adhering, bonding, attaching, sewing together, or the like, of two elements. Two elements will be considered to be joined together when they are integral with one another or joined directly to one another or indirectly to one another, such as when each is directly joined to intermediate elements. "Join" and its derivatives include permanent, releasable, or refastenable joinder. In addition, the joining can be completed either during the manufacturing process or by the end wearer.

The term "layer" when used in the singular can have the dual meaning of a single element or a plurality of elements.

The term "liquid impermeable," when used in describing a layer or multi-layer laminate means that liquid, such as urine, menses or bowel movement, will not pass through the layer or laminate, under ordinary use conditions, in a direction generally perpendicular to the plane of the layer or laminate at the point of liquid contact.

The term "liquid permeable" refers to any material that is not liquid impermeable.

The term "meltblown fibers" refers to fibers formed by extruding a molten thermoplastic material through a plurality of fine, usually circular, die capillaries as molten threads or filaments into a high velocity, usually heated, gas (e.g., air) stream which attenuates the filaments of molten thermoplastic material to reduce their diameter. In the particular case of a coform process, the meltblown fiber stream intersects with one or more material streams that are introduced from a different direction. Thereafter, the meltblown fibers and other materials are carried by the high velocity gas stream and are deposited on a collecting surface. The distribution and orientation of the meltblown fibers within the formed web is dependent on the geometry and process conditions. Under certain process and equipment conditions, the resulting fibers can be substantially "continuous," defined as having few separations, broken fibers or tapered ends when multiple fields of view are examined through a microscope at 10× or 20× magnification. When "continuous" melt blown fibers are produced, the sides of individual fibers will generally be parallel with minimal variation in fiber diameter within an individual fiber length. In contrast, under other conditions, the fibers can be overdrawn and strands can be broken and form a series of irregular, discrete fiber lengths and numerous broken ends. Retraction of the once attenuated broken fiber will often result in large clumps of polymer. Such a process is disclosed, for example, in U.S. Pat. No. 3,849,241 to Butin et al., which is hereby incorporated by reference in a manner that is consistent herewith.

The terms "nonwoven" and "nonwoven web" refer to materials and webs of material having a structure of individual fibers or filaments which are interlaid, but not in an identifiable manner as in a knitted fabric. The terms "fiber" and "filament" are used herein interchangeably. Nonwoven fabrics or webs have been formed from many processes such as, for example, meltblowing processes, spunbonding processes, air laying processes, and bonded-carded-web processes. The basis weight of nonwoven fabrics is usually expressed in ounces of material per square yard (osy) or grams per square meter (gsm) and the fiber diameters are usually expressed in microns. (Note that to convert from osy to gsm, multiply osy by 33.91.)

The term "personal care absorbent article" includes, but is not limited to, absorbent articles such as diapers, diaper pants, baby wipes, training pants, absorbent underpants, child care pants, swimwear, and other disposable garments; feminine care products including sanitary napkins, wipes, menstrual pads, menstrual pants, panty liners, panty shields, interlabials, tampons, and tampon applicators; adult-care products including wipes, pads such as breast pads, containers, incontinence products, and urinary shields; clothing components; bibs; athletic and recreation products; and the like.

The term "polymer" includes, but is not limited to, homopolymers, copolymers, for example, block, graft, random, and alternating copolymers, terpolymers, etc., and blends and modifications thereof. Furthermore, unless otherwise specifically limited, the term "polymer" shall include all possible configurational isomers of the material. These configurations include, but are not limited to, isotactic, syndiotactic, and atactic symmetries.

The terms "spunbond" and "spunbonded fiber" refer to fibers which are formed by extruding filaments of molten thermoplastic material from a plurality of fine, usually circular, capillaries of a spinneret, and then rapidly reducing the diameter of the extruded filaments.

The term "target zone" refers to an area of an absorbent article where it is particularly desirable for the majority of a fluid insult, such as urine, menses, or bowel movement, to initially contact. In particular, for an absorbent article of the present invention, the insult target zone refers to the area of the absorbent core extending a distance equal to 15% of the total length and width of the article from the insult point in all directions.

The term "thermoplastic" describes a material that softens when exposed to heat and which substantially returns to a non-softened condition when cooled to room temperature.

The term "% by weight", "weight %", "wt %" or derivative thereof, when used herein, is to be interpreted as based on the dry weight, unless otherwise specified herein.

These terms may be defined with additional language in the remaining portions of the specification.

DETAILED DESCRIPTION

Absorbent composites of this invention are useful in absorbent articles, such as disposable absorbent articles. An absorbent article of the present invention can have an absorbent core, and can additionally include a topsheet and/or a backsheet, where the absorbent core can be disposed between the topsheet and the backsheet. The articles can further include one or more heat-activatable expandable structures. The heat-activatable expandable structures present in the article have the ability to stay flat before activation, thus reducing the size of the structures and providing for efficient manufacturing, packaging, and/or storage. Upon applying heat to raise the temperature of the heat-activatable expandable structures, the heat-activatable expandable structures expand to a final size suitable for product usage.

To gain a better understanding of the present invention, attention is directed to the figures for exemplary purposes showing a feminine care article of the present invention. It is understood that the present invention is suitable for use with various other personal care absorbent articles without departing from the scope of the present invention.

As representatively shown in FIG. 1, by way of example, the feminine care article 20 can be a feminine care pad or napkin. The article can have a lengthwise, longitudinal direction 22 which can extend along an appointed y-axis of the article, and a transverse, laterally extending, cross direction 24 which can extend along an appointed x-axis of the article. Additionally, the article can include first and second longitudinally opposed end portions 72, and an intermediate portion 76 located between the end portions. Generally stated, the intermediate portion 76 can be the middle 34 percent (%) of an overall, longitudinal length of the article 20. The feminine care pad 20 also has first and second side edges 34 that are the longitudinal sides of the elongated feminine care pad 20.

The side edges 34 can be contoured to match the shape of the article 20. The article 20 can have any desired shape. The feminine care article can, for example, have a dog bone shape, a race track shape, an hourglass shape, or the like. Additionally, the article can be substantially, longitudinally symmetric, or may be longitudinally asymmetric, as desired.

As representatively shown, the longitudinal dimension of the article is relatively larger than the transverse (lateral) dimension of the article. Particular configurations of the absorbent article can include an optional bodyside liner or cover 26 (also referred to as a topsheet), and/or an optional baffle or backsheet 28. The article has a first major surface 21 which forms a body-facing (bodyside) surface and a second major surface 23 disposed distally from the first major surface 21 which forms a garment-facing surface of the absorbent article. In some aspects, a cover is present which can comprise the first major surface 21 of the absorbent article. In some aspects, a backsheet is present which can comprise the second major surface 23 of the article.

Additionally, an absorbent core 30 can be present in the absorbent article. In aspects where a cover and backsheet are present, the absorbent core 30 can be positioned between the cover and backsheet. In desired arrangements, the cover can be liquid-permeable, and the backsheet can be operatively liquid-impermeable. In other arrangements, the backsheet can provide an outercover of the article. As representatively shown, for example, peripheries of the cover and backsheet may be substantially entirely coterminous. Alternatively, the peripheries of the cover 26 and the backsheet 28 may be partially or entirely non-coterminous.

The cover 26 may include a layer constructed of any operative material, and may be a composite material. For example, the cover layer can include a woven fabric, a nonwoven fabric, a polymer film, a film-fabric laminate or the like, as well as combinations thereof. Examples of a suitable nonwoven fabric include spunbond fabric, meltblown fabric, coform fabric, carded web, bonded-carded-web, bicomponent spunbond fabric, or the like, as well as combinations thereof. Other examples of suitable materials for constructing the cover layer can include rayon, bonded-carded webs of polyester, polypropylene, polyethylene, nylon, or other heat-bondable fibers, polyolefins, such as copolymers of polypropylene and polyethylene, linear low-density polyethylene, aliphatic esters such as polylactic acid, finely perforated film webs, net materials, and the like, as well as combinations thereof. In desired arrangements, the cover layer can be configured to be operatively liquid-permeable.

A more particular example of a suitable cover layer material can include a bonded-carded-web composed of polypropylene and polyethylene, such as has been used as a cover stock for KOTEX brand pantiliners, and has been obtainable from Vliesstoffwerk Christian Heinrich Sandler GmbH & Co. KG, a business having an address at Postfach 1144, D95120 Schwarzenbach/Saale, Germany. Other examples of suitable materials are composite materials of a polymer and a nonwoven fabric material. The composite materials are typically in the form of integral sheets generally formed by the extrusion of a polymer onto a web of spunbond material. In a desired arrangement, the cover 26 can be configured to be operatively liquid-permeable with regard to the liquids that the article is intended to absorb or otherwise handle. The operative liquid-permeability may, for example, be provided by a plurality of pores, perforations, apertures or other openings, as well as combinations thereof, which are present or formed in the cover layer. The apertures or other openings can help increase the rate at which bodily liquids can move through the thickness of the cover layer and penetrate into the other components of the article (e.g. into the absorbent core 30).

The selected arrangement of liquid-permeability is desirably present at least on an operative portion of the cover that is appointed for placement on the body side of the article. The cover 26 can provide comfort and conformability, and can function to direct bodily exudates away from the body and toward the absorbent core 30. In a desired feature, the cover 26 can be configured to retain little or no liquid in its structure, and can be configured to provide a relatively comfortable and non-irritating surface next to the body tissues of a female wearer. The cover 26 can be constructed of any material which is also easily penetrated by bodily fluids that contact the surface of the cover layer.

The cover 26 can also have at least a portion of its bodyside surface treated with a surfactant and/or a menses modifier to increase the surface energy of the material surface or reduce the viscoelastic properties of the menses, and to render the cover more hydrophilic and more wettable to body fluids. The surfactant can permit arriving bodily liquids to more readily penetrate the cover layer. The surfactant may also diminish the likelihood that the arriving bodily fluids, such as menstrual fluid, will flow off the cover layer rather than penetrate through the cover layer into other components of the article (e.g., into the absorbent core structure). In a particular configuration, the surfactant can be substantially evenly distributed across at least a portion of the upper, bodyside surface of the cover 26 that overlays the upper, bodyside surface of the absorbent.

The cover 26, if present, may be maintained in secured relation with the absorbent core 30 by bonding all or a portion of the adjacent surfaces to one another. A variety of bonding methods known to one of skill in the art may be utilized to achieve any such secured relation. Examples of such methods include, but are not limited to, the application of adhesives in a variety of patterns between the two adjoining surfaces, entangling at least portions of the adjacent surface of the absorbent with portions of the adjacent surface of the cover, or fusing at least portions of the adjacent surface of the cover to portions of the adjacent surface of the absorbent.

The cover 26 typically extends over the upper, bodyside surface of the absorbent core, but can alternatively extend around the article to partially or entirely surround or enclose the absorbent core. Alternatively, the cover 26 and the backsheet 28 can have peripheral margins which extend outwardly beyond the terminal, peripheral edges of the absorbent core 30 and the extending margins can be joined together to partially, or entirely, surround or enclose the absorbent core.

The backsheet 28 may include a layer constructed of any operative material, and may or may not have a selected level of liquid-permeability or liquid-impermeability, as desired. In a particular configuration, the backsheet 28 may be configured to provide an operatively liquid-impermeable backsheet structure. The backsheet may, for example, include a polymeric film, a woven fabric, a nonwoven fabric, or the like, as well as combinations or composites thereof. For example, the backsheet may include a polymer film laminated to a woven or nonwoven fabric. In a particular feature, the polymer film can be composed of polyethylene, polypropylene, polyester, or the like, as well as combinations thereof. Additionally, the polymer film may be micro-embossed. Desirably, the backsheet 28 can operatively permit a sufficient passage of air and moisture vapor out of the article, particularly out of an absorbent (e.g. storage or absorbent core 30) while blocking the passage of bodily liquids. An example of a suitable backsheet material can include a breathable, microporous film, such as a HANJIN Breathable Backsheet available from Hanjin Printing, Hanjin P&C Company Limited, a business having offices located in Sahvon-li. Junganmvu.Kongiu-City, Chung cheong nam-do, Republic of South Korea. This backsheet material is a breathable film, which is dimple embossed and contains: 47.78% calcium carbonate, 2.22% TiO2, and 50% polyethylene.

In a particular feature, the polymer film can have a minimum thickness of no less than about 0.025 mm, and in another feature, the polymer film can have a maximum thickness of no greater than about 0.13 mm. Bicomponent films or other multi-component films can also be used, as well as woven and/or nonwoven fabrics which have been treated to render them operatively liquid-impermeable. Another suitable backsheet material can include a closed-cell polyolefin foam. For example, closed cell polyethylene foam may be employed. Still another example of a backsheet material would be a material that is similar to a polyethylene film which is used on commercially sold KOTEX brand pantiliners, and is obtainable from Pliant Corporation, a business having offices located in Schaumburg, Ill., U.S.A.

The structure of the absorbent core 30 can be operatively configured to provide desired levels of liquid retention and storage capacity, and desired levels of liquid acquisition and distribution. More particularly, the absorbent core can be configured to hold a liquid, such as urine, bowel movement, menses, other complex liquid, or the like, as well as combinations thereof. The absorbent core can include a matrix of absorbent fibers and/or absorbent particulate material to form a stabilized structure. The absorbent fiber can include natural and/or synthetic fiber. The absorbent core may also include one or more components that can modify menses or intermenstrual liquids.

The absorbent core 30 may also include superabsorbent material. Superabsorbent materials suitable for use in the present invention are known to those skilled in the art, and may be in any operative form, such as particulate form.

Generally stated, the superabsorbent material can be a water-swellable, generally water-insoluble, hydrogel-forming polymeric absorbent material, which is capable of absorbing at least about 10, desirably about 30, and possibly about 60 times or more its weight in physiological saline (e.g., 0.9 wt % NaCl). The hydrogel-forming polymeric absorbent material may be formed from organic hydrogel-forming polymeric material, which may include natural material such as agar, pectin, and guar gum; modified natural materials such as carboxymethyl cellulose, carboxyethyl cellulose, and hydroxypropyl cellulose; and synthetic hydrogel-forming polymers. Synthetic hydrogel-forming polymers include, for example, alkali metal salts of polyacrylic acid, polyacrylamides, polyvinyl alcohol, ethylene maleic anhydride copolymers, polyvinyl ethers, polyvinyl morpholinone, polymers and copolymers of vinyl sulfonic acid, polyacrylates, polyacrylamides, polyvinyl pyridine, and the like. Other suitable hydrogel-forming polymers include hydrolyzed acrylonitrile grafted starch, acrylic acid grafted starch, and isobutylene maleic anhydride copolymers and mixtures thereof. The hydrogel-forming polymers are preferably lightly crosslinked to render the material substantially water insoluble. Crosslinking may, for example, be by irradiation or covalent, ionic, Van der Waals, or hydrogen bonding. Suitable materials are available from various commercial vendors, such as Evonik Stockhausen, Inc., a business having offices located in Greensboro, N.C., U.S.A. The superabsorbent material may desirably be included in an appointed storage or retention portion of the absorbent core, and may optionally be employed in other components or portions of the absorbent article.

The amount of superabsorbent material in a selected layer or other component (e.g., the absorbent core 30) can be at least a minimum of about 1 wt %. The amount of superabsorbent material can alternatively be at least about 5 wt %, and can optionally be at least about 8 wt % to provide improved performance. In other aspects, the amount of superabsorbent material can be up to a maximum of about 75 wt %, or more. The amount of superabsorbent material can alternatively be up to about 35 wt %, and can optionally be up to about 20 wt % to provide improved effectiveness.

If the amount of superabsorbent is outside the desired values, there can be excessive leakage. If the amount of superabsorbent is too high, there can be a poor containment of the superabsorbent gel and an excessive amount of gel on the wearer's skin. Additionally, the transfer of liquid to the absorbent core may be inhibited or the product may have an inadequate rate of liquid intake, causing leakage and excessive wetness against the wearer's skin. The manufacturing costs can also become excessive.

In desired configurations, the absorbent core 30 can be included in a feminine care article and can be configured to provide any operative absorbent capacity. In particular arrangements, for example, the absorbent core can provide a total, overall absorbent saturation capacity of up to about 5 grams of menses stimulant. In other arrangements, the absorbent core can provide a total, overall absorbent saturation capacity which is at least a minimum of about 5.5 grams of menses simulant (5.5 g) (described below). The overall saturation capacity can alternatively be at least about 25 grams, and can optionally be at least about 40 grams of menses simulant to provide improved performance. In a desired arrangement, the total saturation capacity of the absorbent core 30 can be up to about 107 grams of menses simulant, or more.

The specific saturation capacity and the specific retention capacity of the absorbent core 30 can be determined by soaking a 1 inch by 1 inch (2.54 cm×2.54 cm) sample of absorbent material in an amount of menses simulant that is sufficient to fully saturate the sample (e.g., 30 mL) for 30 minutes. The wet absorbent is then placed between a layer of through-air-bonded-carded web material and a layer of blotter paper (both described below), and a pressure of 0.05 psi (0.345 KPa) is applied for 1 minute to remove any pools of liquid. The saturated sample is then weighed. The weight of liquid held in the sample divided by the dry weight of the sample is the specific saturation capacity of the sample.

After the saturated sample is weighed, the absorbent sample is placed in a centrifuge and spun at 300 G for 3 minutes. The spun sample is then weighed. The weight of the liquid remaining in the spun sample divided by the dry weight of the sample is the specific retention capacity of the sample. Accordingly:

Saturation Capacity=(Wet Wt. Before Centrifuge−Dry Wt.)/(Dry Wt.)

Retention Capacity=(Wet Wt. After Centrifuge−Dry Wt.)/(Dry Wt.)

The total absorbent saturation capacity of an overall layer or other component can be determined by multiplying its specific saturation capacity times the total weight of such component. Similarly, total absorbent retention capacity of an overall layer or other component can be determined by multiplying its specific retention capacity times the total weight of such component.

A suitable through-air-bonded-carded web material has a 2.5 osy (84.8 g/m2) basis weight, a 0.024 g/cm$^3$ density, and is composed of 60 wt % of 6 denier, KoSa type 295 polyester fiber; and 40 wt % of 3 denier, Chisso ESC-HR6 bicomponent fiber. The polyester fiber is available from KoSa, a business having offices in Charlotte, N.C., U.S.A., and the bicomponent fiber is available from Chisso Corporation, a business having offices located in Osaka, Japan. A suitable blotter paper for the tests is 100-lb white blotter paper available from Curtis Fine Papers, a business having offices located in Guardbridge, Scotland. Equivalent materials may optionally be employed.

The absorbent core 30 can be provided by a single unitary layer, or can comprise a composite structure having a selected plurality of component strata or layers. In some aspects, the absorbent core 30 is desirably a stabilized structure.

In some aspects, the feminine care pad 20 can include an optional intake layer 32, as seen in FIG. 1 for example. The intake layer 32 can help desorb liquid from the cover 26, and can help manage surges or gushes of liquid entering the article. The intake layer can also help wick or otherwise distribute liquids through the absorbent core. In desired arrangements, the intake layer can provide a temporary storage of liquid, and may provide a selected level of liquid retention. As representatively shown, the intake layer 32 can be operatively joined to the article and may be positioned between the cover 26 and the absorbent core 30.

The intake layer 32 or other supplemental layer may include natural fibers, synthetic fibers, superabsorbent materials, a woven fabric, a nonwoven fabric, a wet-laid fibrous web, a substantially unbonded airlaid fibrous web, an operatively bonded, stabilized-airlaid fibrous web, or the like, as well as combinations thereof. Additionally, the intake layer may include a selected quantity of superabsorbent materials, as desired. In a particular aspect, the fibrous material of the intake layer can be substantially free of debonding agents. The intake layer may also include one or more components that can modify menses or inter-menstrual liquid. In a particular arrangement, the intake layer 32 can be composed of a thermally-bonded, stabilized-airlaid fibrous web (e.g., Concert product code DT200.100.D0001), which is available from Concert Industries, a business having offices located in Gatineaux, Quebec, Canada.

In a desired feature, the intake layer 32 can have a desired basis weight and/or density. In particular aspects, the intake layer 32 can have a basis weight which is at least a minimum of about 30 g/m$^2$. The intake layer basis weight can alternatively be at least about 100 g/m$^2$ and can optionally be at least about 150 g/m$^2$ to provide improved performance. In other aspects, the intake layer basis weight can be up to a maximum of about 250 g/m$^2$, or more. The intake layer basis weight can alternatively be up to about 225 g/m$^2$ and can optionally be up to about 200 g/m$^2$ to provide improved performance.

If the basis weight of the intake layer 32 is outside the desired values, the article can be too thick and bulky, and can provide poor comfort and excessive awareness of the article during use. An overly high basis weight can excessively decrease the amount of liquid transferred to the absorbent core 30, can undesirably increase the amount of liquid held in the intake layer and/or can be excessively expensive. An overly low basis weight can excessively limit the ability to acquire, temporarily store and transfer liquid, and can permit premature leakage. If the basis weight of the intake layer is outside the desired values, the article can also exhibit an excessively high rewet or flowback to the wearer's skin and provide an undesired wet, moist feel to the wearer. Additionally, the intake layer can present an excessively low void volume to subsequent inputs of liquid, and the low void volume can contribute to premature leakage and excessive rewet or flowback to the wearer's skin.

In other aspects, the intake layer 32 can have a density which is at least a minimum of about 0.01 g/cm$^3$. The intake layer density can alternatively be at least about 0.02 g/cm$^3$ and can optionally be at least about 0.04 g/cm$^3$ to provide improved performance. In other aspects, the intake layer density can be up to a maximum of about 0.14 g/cm$^3$, or more. The intake layer density can alternatively be up to about 0.10 g/cm$^3$ and can optionally be up to about 0.08 g/cm$^3$ to provide improved performance.

If the density of the intake layer 32 is outside the desired values, the article can exhibit excessive leakage and can provide an undesired moist, wet feeling against the wearer's skin. An overly high density can limit the saturation capacity of the intake layer and can provide excessively low permeability. This can excessively slow the acquisition and intake of liquid. Additionally, an overly high density can decrease and inhibit the desired liquid transfer to the absorbent core 30. Insufficient liquid transfer can increase rewet or flowback of liquid to the wearer's skin and can decrease the void volume in the intake layer that is available to absorb a follow-up input of liquid, resulting in an increased likelihood of a premature leak. An overly low density can provide an excessively low web tensile strength and can cause web handling problems. Depending on the basis weight, a low density can provide an excessively thick bulky intake layer that can cause poor comfort and excessive awareness of the product. A low intake layer density can also allow discrete amounts of liquid to be immobilized within the intake structure. This liquid can then be available to increase the likelihood of liquid rewet and flowback to the wearer's skin. Additionally, an overly low density intake structure can provide excessively high permeability. As a result, the properties of liquid control, spreading, distribution and temporary storage can be inadequate. The article can also allow premature leakage or an undesirably moist, wet skin.

Additionally, the intake layer 32 can have a specific, absorbent saturation capacity which is at least a minimum of about 10 grams menses simulant per gram of intake layer material (10 g/g). The specific saturation capacity of the intake layer can alternatively be at least about 10.5 g/g and can optionally be at least about 11 g/g to provide improved performance. In other aspects, the specific saturation capacity of the intake layer can be up to a maximum of about 15 g/g, or more. The specific saturation capacity of the intake layer can alternatively be up to about 14.5 g/g and can optionally be up to about 14 g/g to provide improved effectiveness. In a desired arrangement, the specific saturation capacity of the intake layer can be about 13 g/g.

In a further feature, the intake layer 32 can have a total, absorbent saturation capacity which is at least a minimum of about 0.5 grams of menses simulant (0.5 g). The total saturation capacity of the intake layer can alternatively be at least about 5 g and can optionally be at least about 10 g to provide improved performance. In other aspects, the total saturation capacity of the intake layer can be up to a maximum of about 23 g, or more. The total saturation capacity of the intake layer can alternatively be up to about 22 g and can optionally be up to about 21 g to provide improved effectiveness. In a desired arrangement, the total absorbent saturation capacity of the intake layer can be about 17 grams of menses simulant.

The intake layer 32 of the present invention can be equal to or smaller in size, as compared to the size of the absorbent core 30. For example, the intake layer 32 might have a surface area that is approximately 25-50% of the surface area of the absorbent core 30. The intake layer can desirably be substantially centered (in the longitudinal direction 22 and the transverse direction 24 with respect to the absorbent core 30, but it may optionally be skewed or offset in a selected direction (e.g., along the longitudinal direction 22), depending on where the liquid is expected to first enter the absorbent article.

The intake layer 32 may have any operative shape and/or design. For example, the intake layer may include a single piece of material, or multiple pieces of material, such as multiple strips of material. In addition, the intake layer 32 may include holes or apertures to better provide desired liquid-intake properties. The apertures may extend partially or completely through the z-directional thickness of the intake layer 32, as desired.

In some aspects, the article 20 can include at least one side cover (not shown). Side covers are an additional strip of cover material that is positioned longitudinally along a longitudinal side edge of the article. Side covers are often hydrophobic, but they need not be. Suitable materials for side covers include a fibrous material formed from fusible polymeric fibers or filaments. The side cover can be nonperforated, although a perforated web can be used if desired. The side cover can be formed from various polymers, including polyamides, polyesters, polyolefins, polyvinyl acetate, polyvinyl chloride, polyvinyl alcohol, cellulose acetate, viscose, and the like. Suitable materials include polypropylene spunbond and bonded carded webs. In some aspects, the side cover has a uniform web with a denier of about 1.5 or greater. Side covers are also discussed in U.S. Pat. No. 5,415,640 to Kirby et al., which is incorporated herein by reference in a manner that is consistent herewith.

In some aspects of the invention, the article 20 can include a system of side panel or wing portions 42. The side panels can be unitarily formed from a selected component of the article, such as the cover and/or the backsheet, and are integrally connected to appointed sections of the side regions along the intermediate portion 76 of the article. Alternatively, the side panels or wings can be separately provided members that are subsequently attached or otherwise operatively joined to the intermediate portion of the article 20.

The side panels can have an appointed storage position (not shown) in which the side panels 42 are directed generally inwardly toward the longitudinally-extending centerline 52. In some aspects, the side panel that is connected to one side margin may have sufficient cross-directional length to extend and continue past the centerline 52 to approach the laterally opposite side margin of the article. The storage position of the side panels can ordinarily represent an arrangement observed when the article is first removed from its wrapper or other packaging. Prior to placing the article into a bodyside of an undergarment prior to use, the side panels 42 can be selectively arranged to extend laterally from the side regions of the article intermediate portion 76. After placing the article in the undergarment, the side panels 42 can be operatively wrapped and secured around the side edges of the undergarment to help hold the article in place, in a manner well known in the art.

The side panel portions 42 can have any operative construction and can include a layer of any operative material. Additionally, each side panel can comprise a composite material. For example, the side panels may include a spunbond fabric material, a bi-component spunbond material, a necked spunbond material, a neck-stretched-bonded-laminate (NBL) material, a meltblown fabric material, a bonded carded web, a thermal bonded carded web, a through-air bonded carded web, or the like, as well as combinations thereof.

Each side panel 42 can be joined to its corresponding side region of the article in any operative manner. For example, the side panel can be joined to the cover 26, the backsheet 28 or another article component, as well as any combination thereof. As seen in FIGS. 1-1B, for example, each side panel 42 is joined to the outward, garment-side surface of the backsheet 28, but may optionally be joined to the bodyside surface of the backsheet. The side panel can be attached with hot melt adhesive, but any other operative adhesive or attachment mechanism may alternatively be employed.

In another feature, each side panel portion 42, or any desired combination of the employed side panel portions, can include a panel-fastener component which is operatively joined to an appointed engagement surface of its associated side panel. The panel-fastener component can include a system of interengaging mechanical fasteners, a system of adhesive fasteners, or the like, as well as combinations thereof.

As representatively shown in FIGS. 1-1B, for example, each side panel 42 can include a cooperating component of an interengaging mechanical fastener system. As illustrated, the component can be a "male" component 46 (e.g., a hook component) of the fastener system. Any operative hook component may be employed. For example, a suitable hook component material can include a J-hook, mushroom-head hook, flat-top nail-head hook, a palm-tree hook, a multiple-J hook, or the like, as well as combinations thereof. Alternatively, either or both side panels 42 can include a panel-fastener system which incorporates an operative adhesive. The adhesive may be a solvent-base adhesive, a hot melt adhesive, a pressure-sensitive adhesive, or the like, as well as combinations thereof.

An operative first section of the selected hook component 46 can be joined to a major facing surface of at least a first side panel portion 42 and can be configured to contact or otherwise engage a second side panel portion during ordinary use. Additionally, an operative second section of a hook component, composed of the same or different type of hook material, can be joined to a major facing surface of the second side panel portion and can be configured to contact or otherwise engage an outward surface of the wearer's undergarment during ordinary use. For example, the hook component can be arranged to operatively engage and removably attach to the outward surface of a crotch region of the undergarment.

Each side panel portion 42, or any desired combination of the employed side panel portions, can include a loop or other "female" component 48 of an interengaging mechanical fastener system. Any operative loop component may be employed. For example, a suitable loop component material can include a woven fabric, a knit fabric, a nonwoven fabric, a fabric laminated to a substrate, or the like, as well as combinations thereof.

An operative first section of a selected loop component 48 can be joined to a major facing surface of at least the second side panel portion and can be configured to contact or otherwise engage the hook component 46 on the first side panel portion 42 during ordinary use. Additionally, an operative second section of a loop component, composed of the same or different type of loop material, can be joined to a major facing surface of the first side panel portion 42. As a result, the user can have the option of alternatively attaching the second hook component of the second side panel onto the second loop component of the first side panel. Accordingly, the hook component 46 may alternatively be engaged with the outward surface of the wearer's undergarment.

Each or any desired combination of the provided loop components 48 may be a separately provided member that is subsequently joined and assembled to its corresponding side panel portion 42. In a desired feature, each or any desired combination of the provided loop components can be integrally provided by the material employed to construct its corresponding side panel portion.

In the various arrangements of the present invention, the hook component 46 can be configured to have a particularly selected hook concentration or density (hooks per unit area). In a particular aspect, the hook density can be at least a minimum of about 1500 hooks/in$^2$ (about 232 hooks/cm$^2$). The hook density can alternatively be at least about 2000 hooks/in$^2$ (about 310 hooks/cm$^2$) and can optionally be at least about 3000 hooks/in$^2$ (about 465 hooks/cm$^2$) to provide improved performance. In another aspect, the hook density can be no more than a maximum of about 7000 hooks/in$^2$ (about 1085 hooks/cm$^2$). The hook density can alternatively be not more than about 6000 hooks/in$^2$ (about 930 hooks/cm$^2$) and can optionally be not more than about 5000 hooks/in$^2$ (about 775 hooks/cm$^2$) to provide improved performance.

Examples of suitable hook materials can include 85-Series and 61-Series hook materials available from Velcro, U.S.A., a business having offices located in Manchester, N.H., U.S.A. The hook materials can have a hook density of about 775 hooks/cm$^2$.

In a particular aspect, the material of the loop component 48 may include a nonwoven fabric having continuous bonded areas defining a plurality of discrete unbonded areas. The fibers or filaments within the discrete unbonded areas of the fabric are dimensionally stabilized by the continuous bonded areas that encircle or surround each unbonded area, such that no support or backing layer of film or adhesive is required. The unbonded areas are specifically designed to afford spaces between fibers or filaments within the unbonded area that remain sufficiently open or large to receive and engage hook elements of the complementary hook material. In particular, a pattern-unbonded nonwoven fabric or web may include a spunbond nonwoven web formed of single component or multi-component melt-spun filaments. At least one surface of the nonwoven fabric can include a plurality of discrete, unbonded areas surrounded or encircled by continuous bonded areas. The continuous bonded areas dimensionally stabilize the fibers or filaments forming the nonwoven web by bonding or fusing together the portions of the fibers or filaments that extend outside of the unbonded areas into the bonded areas, while leaving the fibers or filaments within the unbonded areas substantially free of bonding or fusing. The degree of bonding or fusing within the bonding areas desirably is sufficient to render the nonwoven web non-fibrous within the bonded areas, leaving the fibers or filaments within the unbonded areas to act as "loops" for receiving and engaging hook elements. Examples of suitable point-unbonded fabrics are described in U.S. Pat. No. 5,858,515 entitled Pattern-Unbonded Nonwoven Web and Process for Making the Same, by T. J. Stokes et al., and granted Jan. 12, 1999; the entire disclosure of which is hereby incorporated by reference in a manner that is consistent herewith.

The complementary components of the mechanical fastener are configured to provide a selected attachment peel-force value. In a particular aspect, the peel-force value can be at least a minimum of about 75 grams (g). The peel-force value can alternatively be at least about 100 g and can optionally be at least about 150 g to provide improved performance. In other aspects, the peel-force value can be up to a maximum of about 300 g, or more. The peel-force value can alternatively be up to about 250 g and can optionally be up to about 225 g to provide improved effectiveness.

The complementary components of the mechanical fastener are also configured to provide a selected attachment shear-force value. In a particular aspect, the shear-force value can be at least a minimum of about 1000 g. The shear-force value can alternatively be at least about 1250 g and can optionally be at least about 1500 g to provide improved performance. In other aspects, the shear-force value can be up to a maximum of about 3500 g, or more. The shear-force value can alternatively be up to about 3000 g and can optionally be up to about 2000 g to provide improved effectiveness.

If the peel-force and/or the shear-force are outside the desired values, the fasteners may experience premature unfastening, or may be too difficult to unfasten to remove the article 20 from an associated undergarment.

In the construction of the article 20, the various components may be assembled and held together with any operative securement mechanism or system. For example, the desired attachments or securements can include adhesive bonds, cohesive bonds, thermal bonds, ultrasonic bonds, pins, snaps, staples, rivets, stitches, welds, zippers, or the like, as well as combinations thereof.

Figure 1A:
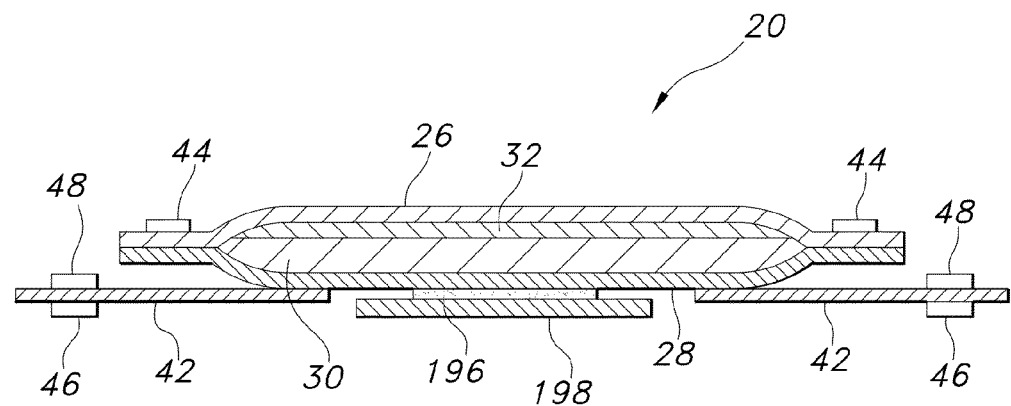
FIG. 1A is a cross-section view of the article of FIG. 1 prior to heat-activation taken along line 53-53.
Figure 1B:
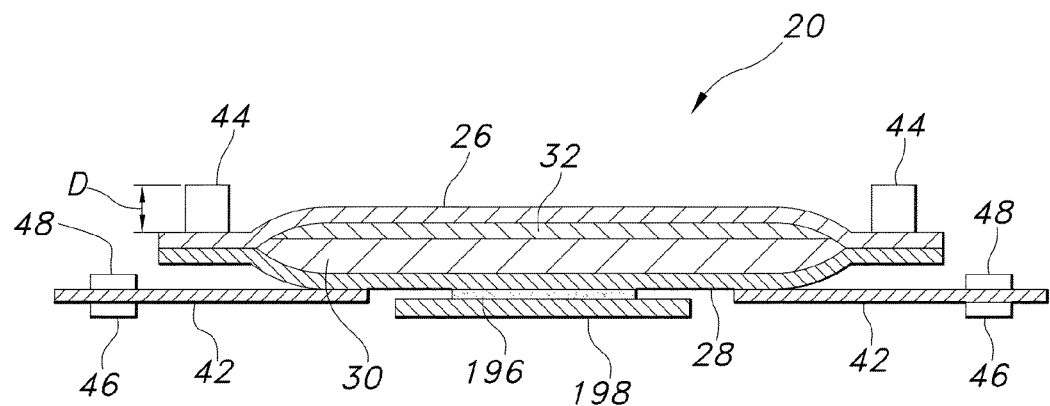
FIG. 1B is a cross-section view of the article of FIG. 1 after heat-activation taken along line 53-53.

Additionally, as seen in FIGS. 1A-B, a selected configuration (e.g., one or more strip regions) of a garment attachment mechanism (e.g., a garment-attachment adhesive 196) may be distributed onto the garment-side of the article to help secure the article to a wearer's undergarment. Typically, the garment adhesive is distributed over the garment-side of the backsheet 28, and one or more layers or sheets of release material 198 are removably placed over the garment adhesive to cover the adhesive for storage prior to use. Optionally, the garment-attachment mechanism can include an operative component of a mechanical fastening system. For example, the garment-attachment mechanism can include an operative component of a "hook-and-loop" type of fastening system.

The article of the present invention includes at least one heat-activated expandable structure. The heat-activated expandable structure can be in the form of an ink, yarn, fiber, filament, tape, film, nonwoven, laminate, and the like. The heat-activated expandable structure may be positioned suitably on or between various layers of the absorbent product. When positioned between layers of the absorbent product, after expansion of the heat-activated expandable structure, the heat-activated expandable structure serves to separate the layers immediately adjacent the heat-activated expandable structure, thus providing an open space, void, or channel between the layers adjacent the expanded structure. Thus, suitable placement of the heat-activated expandable structures will provide fluid flow channels that will enhance absorbency by directing the flow of liquid to specific areas of the product and minimize overflow of the liquid. Further, since the heat-activatable expandable structures may be of various colors, the structures may be used to additionally provide a visually distinctive appearance to the product. As a further benefit, the heat-activatable expandable structures provide an opportunity to modify fluid handling characteristics, such as, for example, intake, absorbency, and rewet properties, without having to provide an additional material layer to the product. Application of the heat-activatable expandable structures may be used to fine-tune the properties of standard materials used to make products that require different properties.

In one aspect of the invention, the feminine care pad 20 shown in FIGS. 1, 1A-B, 2, and 2A-C is provided with at least one heat-activatable expandable structure 44. Referring to FIGS. 1 and 1A-B, the heat-activatable expandable structure 44 is positioned on the first major surface 21 and extends generally along the side edges 34 of the first major surface. In yet another aspect of the invention, one or more heat-activatable expandable structures 44 can be placed around a target zone 88 of the pad 20. For example, a single heat-activatable expandable structure 44 as in FIG. 1 (although there could be more than one) is in the form of a race track-like shape. Desirably, the heat-activatable expandable structure 44 surrounds, yet leaves exposed, the target zone 88. When the heat-activatable expandable structure 44 is heated, the heat-activatable expandable structure 44 expands to form a walled fluid containment region that prevents fluid leakage towards the front, rear and sides. In use, the heat-activatable expandable structure will inhibit flow of fluids from the target zone 88 to the side edges 34 of the product 20, thus inhibiting fluid leakage from the product. The heat-activatable expandable structure 44 can form any shape that is desired. For example, in one aspect, the heat-activatable expandable structure 44 has a shape that generally matches the shape of the article 20, such as seen in FIG. 1. In another aspect, the one or more heat-activatable expandable structures 44 may be open (not shown) at one or more of the end portions 72 or side edges 34 of the product 20.

Figure 2:
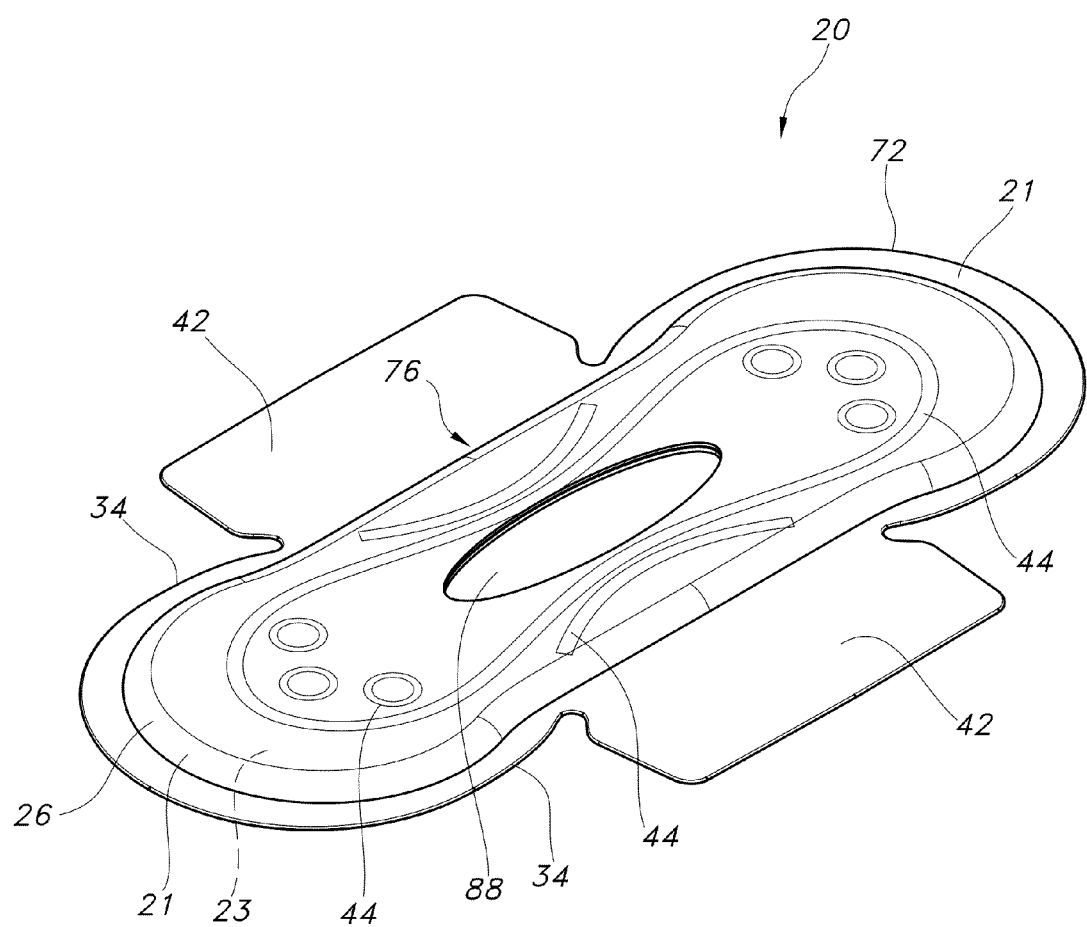
FIG. 2 is a perspective view of another embodiment of the absorbent article of the present invention.
Figure 2A:
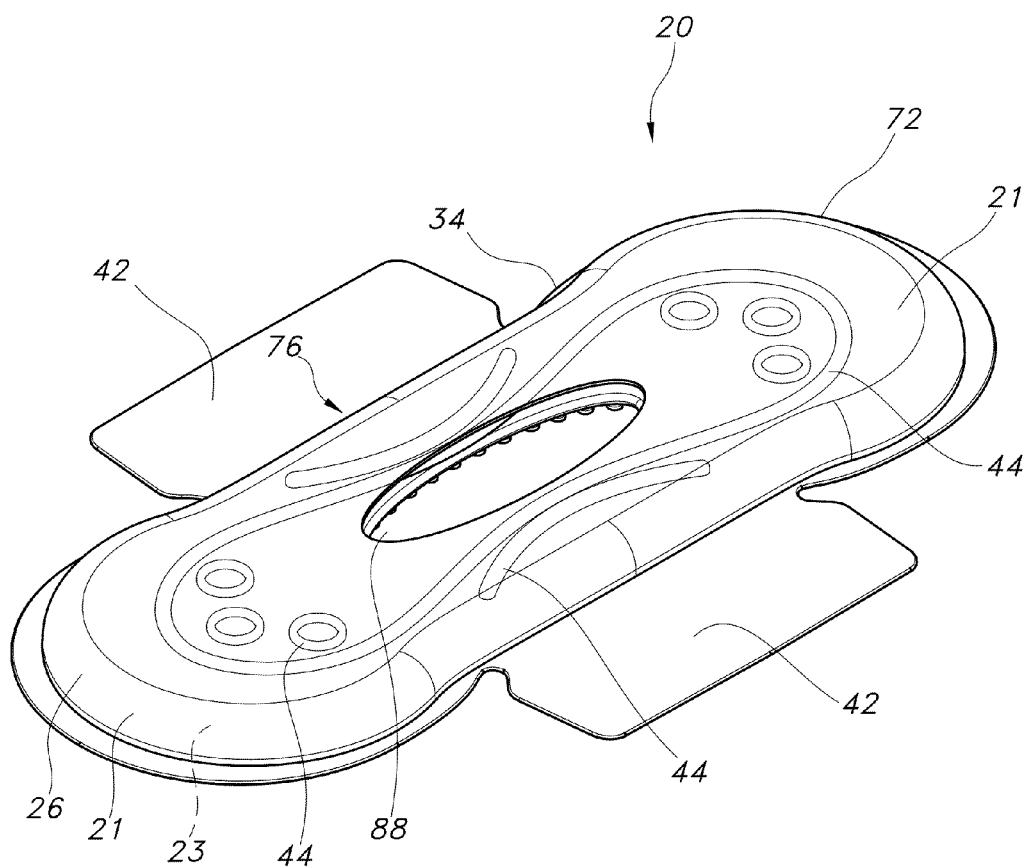
FIG. 2A is the same perspective view of the absorbent article of FIG. 2 after heat-activation.
Figure 2B:
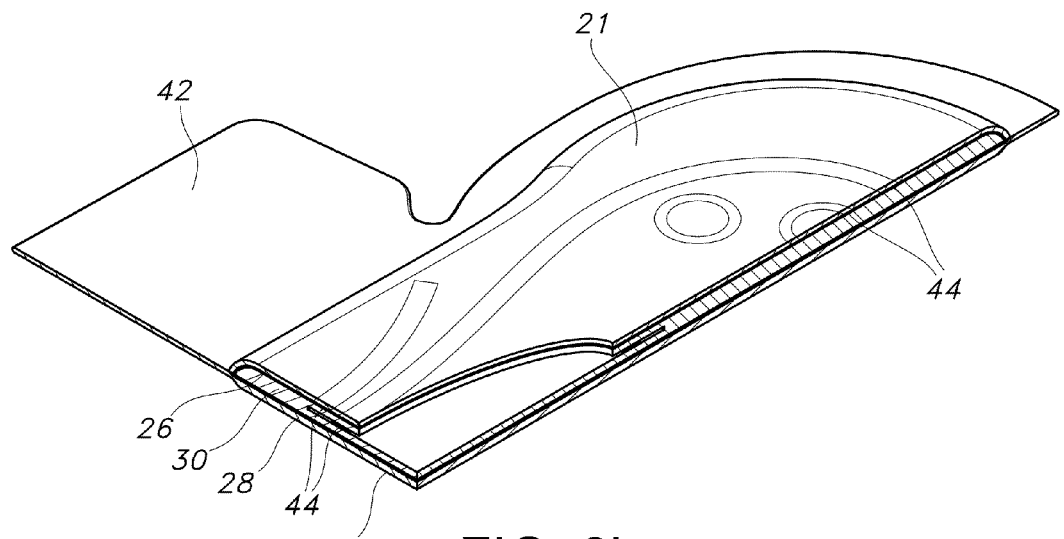
FIG. 2B is a close-up view of a portion of the absorbent article of FIG. 2 prior to activation.
Figure 2C:
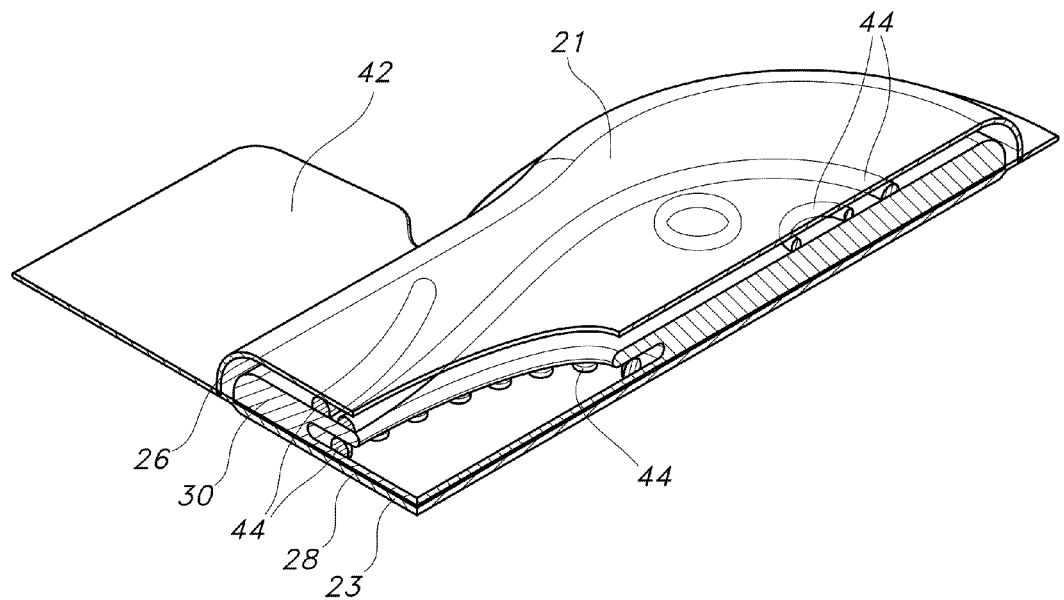
FIG. 2C is the same close-up view of FIG. 2B after heat-activation.

In some aspects, the heat-activatable expandable structure 44 is located on top of the first major surface 21, such as above the cover 26, if present. In other aspects, such as shown in FIGS. 2B and 2C, the heat-activatable expandable structure 44 is located below the first major surface, such as when the heat-activatable expandable structure 44 is integrated into the article 20. For example, in aspects where a cover is present, the heat-activatable expandable structure 44 can be located between the cover 26 and the backsheet 28, or between the cover 26 and the absorbent core 30, or between the cover 26 and optional transfer layer 32. Other configurations for the heat-activatable expandable structure 44 in the article 20 may also be desirable and would be readily apparent to those skilled in the art. Advantageously, placement of the heat-activatable expandable structures 44 between the various layers of the product may create channels between the layers after activation. The channels enhance fluid management by channeling fluid to otherwise remote regions of the product.

In one aspect, the heat-activatable expandable structure may be on the surface of a nonwoven sheet material. In one embodiment, the nonwoven sheet material with the heat-activatable expandable structure may provide a dryness benefit demonstrated by improved fluid intake and rewet properties (test defined below) as compared to the nonwoven sheet material without the heat-activatable expandable structure. For example, the nonwoven sheet material with the heat-activatable expandable structure can exhibit a first and/or second intake rate improvement of up to about 5 seconds, such as up to about 8 seconds, when measured according to the intake rate test method described herein. As another example, the nonwoven sheet material with the heat-activatable expandable structure can exhibit a rewet property value of less than about 1.1 grams, such as less than about 1.0 grams, or such as between about 0.6 grams and about 1.1 grams, when measured according to the rewet test method described herein. In another aspect, the heat-activatable expandable structure comprises from about 0.5 weight percent to about 50 weight percent of the weight of the nonwoven material, or from about 0.5 weight percent to about 25 weight percent of the nonwoven material, or from about 0.5 weight percent to about 10 weight percent of the nonwoven material.

The heat-activatable expandable structure 44 may be liquid pervious, semi-pervious, or liquid impervious, and may be absorbent or nonabsorbent, as desired. Thus, in one aspect of the present invention, when the heat-activatable expandable structure 44 is absorbent, it can provide additional absorbent capacity in the article 20. In still other embodiments, at least one heat-activatable expandable structure 44 can be disposed at various other locations on the article 20, such as oriented in the transverse-extending direction located a distance from one side or another side of the transverse-extending centerline 53 of the article 20, or in a diagonal direction, or any other suitable orientation as desired.

The heat-activatable expandable structure 44 may be of any suitable width and may be dependent on the size of the article. However, in some desirable aspects, the width of the heat-activatable expandable structure 44 is greater than about 1 millimeters (mm), or greater than about 2 mm or less, or greater than about 3 mm. As another example, the width of the heat-activatable expandable structure 44 may be from about 1 to about 25 mm, or from about 2 to about 20 mm, or from about 3 to about 15 mm.

The heat-activatable expandable structure 44 can be any length as desired and may be dependent on the size of the article. Although the heat-activatable expandable structure 44 may have a length that is only a portion of the length of the feminine care pad 20, in other aspects, the heat-activatable expandable structure 44 can be made up to the full length of the feminine care pad 20. For example, the heat-activatable expandable structure 44 can range in length from about 25 mm to about 270 mm, such as from about 50 mm to about 200 mm to provide improved performance. In one particular aspect, the length of the heat-activatable expandable structure 44 is about 110 mm.

In general, the heat-activatable expandable structure 44 should be soft and flexible enough so that the absorbent article is comfortable to wear. However, the heat-activatable expandable structure 44 should also be stiff enough to maintain leakage barrier properties when activated. In one aspect, the heat-activatable expandable structure 44 may have a rubbery texture that advantageously creates a gasket effect upon contact with the skin surface.

In some aspects, the heat-activatable expandable structure 44 is attached to the body-facing side of the cover 26 (if present), such as seen in FIGS. 1 and 1A-B. In other aspects, the heat-activatable expandable structure 44 can be attached to the garment-facing side of the cover 26 such that the cover 26 is located over the heat-activatable expandable structure 44. In still other aspects, the heat-activatable expandable structure 44 is attached to one of the various other layers or components of the pad 20, such as the absorbent core 30 for example, such as seen in FIGS. 2 and 2A-C. Attachment of the heat-activatable expandable structure 44 to a component surface can be accomplished using bonding techniques known in the art including, but not limited to, adhesive bonds, cohesive bonds, thermal bonds, ultrasonic bonds, stitching, or the like, and combinations thereof. In one desirable aspect, the heat-activatable expandable structure 44 is printed onto the component to which it is attached.

Suitable materials for the heat-activatable expandable structure 44 include heat-activatable expandable inks, such as Aqua Puff inks obtainable from Polytex Environmental inks. Aqua Puff inks are expandable inks which react when exposed to heat to produce a gas by-product that causes the ink to expand or "puff up". Suitable Aqua Puff inks include Puff Ink MW 4319 and MW 4404. Expandable inks can be applied using flexography, gravure, offset, inkjet (digital), curtain, knife and roll coating, silk screen, and rotary screen printing techniques as are well known in the art. The printing of the inks can occur at a number of steps in the converting process, such as on an off-line printing step, or on-line during the product assembly process. Further, the ink can be printed at one process step, and expanded by heat activation at a downstream step. It is believed that a more efficient process may be achieved by not linking the printing step with the heat-activation step.

In some aspects, the heat-activatable expandable structure 44 can include an optional amount of moisture absorbing polymer. The polymer can be present in the heat-activatable expandable structure 44 in an amount as desired, provided that it does not diminish the effectiveness of the heat-activatable expandable structure 44. For example, in some aspects, the heat-activatable expandable structure 44 can contain up to about 1 wt %, such as up to about 5 wt %, or even up to about 10 wt % or more moisture absorbing polymer to provide improved benefits. Examples of suitable moisture absorbing polymers include, but are not limited to, polyethylene oxide, polyethylene glycol, polyvinyl alcohol, polyvinyl pyrolidone, polyvinyl pyridine, or mixtures thereof.

In some aspects, the heat-activatable expandable structure 44 can include an optional elastomeric polymer. The elastomeric polymer may have permeability for water vapor which can facilitate moisture absorption. Further, the elastomeric polymer may add resilience or flexibility to the heat-activatable expandable structure 44. The elastomeric polymer component should be present in an amount which is effective to achieve the desired dimensional change properties. The elastomeric polymer can be present in an amount as desired, provided that it does not diminish the effectiveness of the heat-activatable expandable structure 44. For example, in some aspects, the heat-activatable expandable structure 44 can contain up to about 1 wt %, such as up to about 5 wt %, or even up to about 10 wt % or more elastomeric polymer to provide improved benefits. Examples of suitable elastomeric polymers include, but are not limited to, thermoplastic polyurethanes, poly(ether-amide) block copolymers, thermoplastic rubbers such as uncrosslinked polyolefins, styrene-butadiene copolymers, silicon rubbers, synthetic rubbers such as nitrile rubber, styrene isoprene copolymers, styrene ethylene butylenes copolymers, butyl rubber, nylon copolymers, spandex fibers comprising segmented polyurethane, ethylene-vinyl acetate copolymer or mixtures thereof.

Additionally, adhesion promoters can be added to the heat-activatable expandable structure 44. For example, Carboset 514H, available commercially from Noveon, Inc. of Cleveland, Ohio, is an acrylic colloidal dispersion polymer supplied in ammonia water, which can dry to a clear, water-resistant, non-tacky thermoplastic film.

In addition, the heat-activatable expandable structure 44 can generally contain a coloring agent (e.g., pigment or dye), a solvent, and any other desired ingredients. Typically, a pigment refers to a colorant based on inorganic or organic particles which do not dissolve in water or solvents. Usually pigments form an emulsion or a suspension in water. On the other hand, a dye generally refers to a colorant that is soluble in water or solvents.

The pigment or dye in the heat-activatable expandable structure 44 can be present in an amount effective to be visible once applied to the substrate. For example, the pigment or dye can be present in the ink composition at concentration between about 0.25% to about 40% based on the dry weight basis, and preferably between greater than or equal to about 1% and less than or equal to about 10%.

Suitable organic pigments, include dairylide yellow AAOT (for example, Pigment Yellow 14 CI No. 21 095), dairylide yellow AAOA (for example, Pigment Yellow 12 CI No. 21090), Hansa Yellow, CI Pigment Yellow 74, Phthalocyanine Blue (for example, Pigment Blue 15), lithol red (for example, Pigment Red 52:1 CI No. 15860:1). toluidine red (for example. Pigment Red 22 CI No. 12315), dioxazine violet (for example, Pigment Violet 23 CI No. 51319), phthalocyanine green (for example, Pigment Green 7 CI No. 74260), phthalocyanine blue (for example, Pigment Blue 15 CI No. 74160), naphthoic acid red (for example, Pigment Red 48:2 CI No. 15865:2). Inorganic pigments include titanium dioxide (for example, Pigment White 6 CI No. 77891), carbon black (for example, Pigment Black 7 CI No. 77266), iron oxides (for example, red, yellow. and brown), ferric oxide black (for example, Pigment Black 11 CI No. 77499), chromium oxide (for example, green), ferric ammonium ferrocyanide (for example, blue), and the like.

Suitable dyes that may be used include, for instance, acid dyes, and sulfonated dyes including direct dyes. Other suitable dyes include azo dyes (e.g., Solvent Yellow 14, Dispersed Yellow 23, and Metanil Yellow), anthraquinone dyes (e.g., Solvent Red 111, Dispersed Violet 1, Solvent Blue 56, and Solvent Orange 3), xanthene dyes (e.g., Solvent Green 4, Acid Red 52, Basic Red 1, and Solvent Orange 63), azine dyes (e.g., Jet Black), and the like.

The heat-activatable expandable structure 44 may be applied to the absorbent article generally dispersed or dissolved in a low viscosity carrier. Exemplary solvents are aliphatic hydrocarbons with common binder types, such as polyamide, shellac, nitro-cellulose, and styrene-maleic. Generally, solvent-based treatments include non-catalytic, block urethane resin, which generally demonstrate superior durability over traditional flexographic binders, such as styrene-maleic, rosin-maleic, and acrylic solutions. Desired solvent blends include various acetates such as ethyl acetate, N-propyl acetate, isopropyl acetate, isobutyl acetate, N-butyl acetate, and blends thereof; various alcohols including ethyl alcohol, isopropyl alcohol, normal propyl alcohol, and blends thereof; and glycol ethers including Ektasolve® EP (ethylene glycol monopropyl ether), EB (ethylene glycol monobutyl ether), DM (diethylene glycol monomethyl ether), DP (diethylene glycol monopropyl ether), and PM (propylene glycol monomethyl ether), which may be obtained from Eastman Chemical of Kingsport, Tenn. Other glycols that may also be used are DOWANOL® obtainable from Dow Chemical of Midland, Mich. A desired solvent blend may be a blend of about 50 percent to about 75 percent glycol ether, about 25 percent to about 35 percent N-propyl acetate, and about 15 percent to about 25 percent N-butyl acetate.

Suitable water-based heat-activatable expandable treatments that may be used may further include emulsions that may be stabilized in water-ammonia and may further comprise alcohols, glycols, or glycol ethers as co-solvents. Generally, organic solvents (less than or equal to about 7 percent) may be added to water-based treatments: alcohols, for example, propan-2-ol may be added for speeding up drying and assisting wetting, glycols, for example, mono propylene glycol to slow down drying, glycol ethers, for example, dipropyl glycol mono methyl ether to aid film formation. Such solvents may be commodity chemicals, commercially available from various companies. Generally, water-based treatments include self-crosslinking acrylic copolymer emulsion, which may have demonstrated superior durability over traditional non-crosslinking binders such as acrylic solutions and dispersion copolymers. Besides the solvent and pigments, the heat-activatable expandable treatment may comprise a binder or mixtures thereof. The binder helps stabilize the pigment onto the cover layer 12. Generally, the pigment-to-binder ratios is typically from 1:20 to 1:2.

Waxes may also be included in the heat-activatable expandable structure 44 to increase the slip and improve the rub-resistance of the heat-activatable expandable treatment of the printed polyolefin substrate. Common classifications of waxes include animal (for example, beeswax and lanolin), vegetable (for example, carnauba and candellilia), mineral (for example, paraffin and microcrystalline), and synthetic (for example. Polyethylene, polyethylene glycol, and Teflon®). In one embodiment, a wax can be present in an amount of about 0.5 percent to about 5 percent based on the total heat-activatable expandable structure formulation.

The composition of the heat-activatable expandable structure 44 chosen should, of course, be safe for human use and should not have environmentally deleterious effects. Moreover, it is desirable that the composition is suitable for the intended application process and is preferably temperature resistant to the process employed for forming the absorbent article, e.g., the temperatures used during a vacuum aperturing process and the like elevated heating processes.

Additional, or multiple, heat-activatable expandable structures can each comprise the same material, or they can comprise different materials. As the heat-activatable expandable inks are available in a variety of colors, in some aspects the inks may be used to additionally provide a visually distinctive multi-color appearance to the product. Use of combinations of colors and patterns can create visual cues that provide different signals to a user, for example, degrees of protection, comfort, and/or effectiveness, and so forth. Changes to these patterns and colors could be as easy as changing the ink and printing plate, which are much more economical and quicker than other methods of patterning, e.g., embossing. Alternatively, various patterns and colors may be used to accentuate other elements on the product, e.g., embossing patterns.

The heat-activatable expandable structure 44 is capable of being activated to its desired shape upon application of sufficient heat to the heat-activatable expandable structure. The heat-activatable expandable structure 44, upon exposure to heat, will expand or grow in size. Application of the heat may occur by any suitable means, such as for example, treatment with a hot air stream, passing through a heat tunnel, contact with a hot surface, e.g. a steam can, iron, and so forth, treatment with infrared radiation, treatment with microwaves, and so forth.

Suitably, the heat-activatable expandable structures are capable of expanding in volume by greater than about 1000%, or greater than about 2000%, or greater than about 3000%. As further examples, the heat-activatable expandable structures may be capable of expanding in volume from about 100% to about 6000%, or from about 500% to about 5000%, or from about 1000 to about 4500%.

When heat is applied to the heat-activatable expandable structures, the heat-activatable expandable structures expand in volume, rising a distance D. The distance D will vary as desired, and will vary with various structure designs. For example, the distance D that a given heat-activatable expandable structure 44 will expand can be at least about 0.1 millimeter (mm), such as at least about 0.5 mm, or at least about 1 mm or more to provide improved benefits. As further examples, the heat-activatable expandable structure will expand from about 0.1 mm to about 10 mm, or from about 0.2 mm to about 6 mm, or from about 0.5 mm to about 5 mm. The distance of expansion can be modified as desired according to several factors, including the expanding ability of the heat-activatable material, the temperature reached, and the amount of time the material is heated and so forth. In one aspect, different heat-activatable expandable structures in the product may be constructed of different heat-activatable expandable materials to create heat-activatable expandable structures of varying height. For example, the height or thickness of the heat activatable expandable structure 44 can be greater than about 0.1 millimeter (mm), such as greater than about 0.5 mm, or greater than about 1 mm or more to provide improved benefits. As further examples, the heat-activatable expandable structure may have a height or thickness from about 0.1 mm to about 10 mm, or from about 0.2 mm to about 6 mm, or from about 0.5 mm to about 5 mm.

Suitably, the heat-activatable expandable structures are expanded by heating the structures to a temperature greater than about 100° F., or greater than about 140° F. or greater than about 180° F. As further examples, the heat-activatable expandable structures are expanded by heating the structures to a temperature from about 100° F. to about 350° F., or from about 140° F. to about 330° F., or from about 180° F. to about 300° F.

Suitably, the heat-activatable expandable structures are expanded by maintaining the structures at the desired temperature for a period of time greater than about 0.5 seconds, or greater than about 1.0 seconds, or greater than about 1.5 seconds. As further examples, the heat activatable expandable structures are expanded by maintaining the structures at the desired temperature for a period of time from about 0.5 seconds to about 20 seconds, or from about 1.0 seconds to about 10 seconds, or from about 1.5 seconds to about 8 seconds.

In the preceding various aspects described above, if the heat-activatable expandable structure 44 is located under the cover 26 or other layer of the article 20, then it is desirable in some aspects that that the cover 26 or other layer is operatively affixed to the pad 20 to allow for upward movement of the heat-activatable expandable structure 44 when heat is applied. A stretchable cover or other layer, as discussed above, can also be suitable for such aspects.

In optional arrangements, the article 20 may include additional components or component layers, as desired. For example, a transfer layer may be positioned between the intake layer 32 and the absorbent core 30. The article can also have various other configurations, including a de-coupled configuration and those described in U.S. Patent Application Publication No. 2009/0204095 to McDaniel, which is incorporated herein by reference in a manner that is consistent herewith. Still other article configurations can include folded structures, such as "V" and "W" structures, including those disclosed in U.S. Pat. No. 6,521,811 to Lassen et al., which is incorporated herein by reference in a manner that is consistent herewith.

Figure 3:
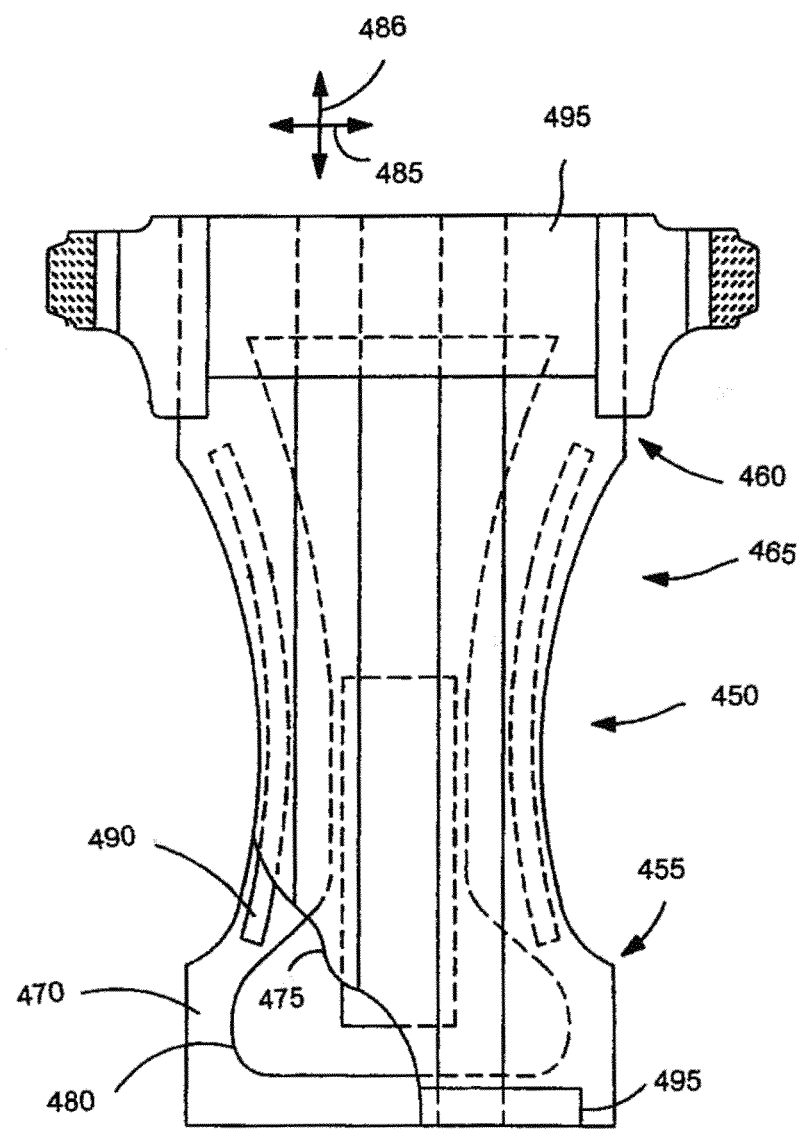
FIG. 3 is a perspective view of a personal care product that may be formed in accordance with one embodiment of the present invention.

In some embodiments, the heat activatable expandable structures may be suitable applied to gasketing materials located at a leg opening or a waist opening of an absorbent product. Referring to FIG. 3, for example, one embodiment of a disposable diaper 450 is shown that generally defines a front waist section 455, a rear waist section 460, and an intermediate section 465 that interconnects the front and rear waist sections. The front and rear waist sections 455 and 460 include the general portions of the diaper which are constructed to extend substantially over the wearer's front and rear abdominal regions, respectively, during use. The intermediate section 465 of the diaper includes the general portion of the diaper that is constructed to extend through the wearer's crotch region between the legs. Thus, the intermediate section 465 is an area where repeated liquid surges typically occur in the diaper.

The diaper 450 includes, without limitation, an outer cover, or backsheet 470, a liquid permeable bodyside liner, or topsheet, 475 positioned in facing relation with the backsheet 470, and an absorbent core body, or liquid retention structure, 480, such as an absorbent pad, which is located between the backsheet 470 and the topsheet 475. The backsheet 470 defines a length, or longitudinal direction 486, and a width, or lateral direction 485 which, in the illustrated embodiment, coincide with the length and width of the diaper 450.

To provide improved fit and to help reduce leakage of body exudates from the diaper 450, the diaper side margins and end margins may be elasticized with suitable elastic members, as further explained below. For example, as representatively illustrated in FIG. 3, the diaper 450 may include leg elastics 490 constructed to operably tension the side margins of the diaper 450 to provide elasticized leg bands which can closely fit around the legs of the wearer to reduce leakage and provide improved comfort and appearance. Waist elastics 495 are employed to elasticize the end margins of the diaper 450 to provide elasticized waistbands. The waist elastics 495 are configured to provide a resilient, comfortably close fit around the waist of the wearer. The heat activatable expandable structures of the present invention may be suitably applied to a facing material in an elastic laminate used as the leg elastics 490 and waist elastics 495 to enhance the gasketing effect against a user's skin, i.e., to reduce leakage at the leg or the waist.

The present invention may be better understood with reference to the following examples.

Intake rates and desorption was measured for materials treated with heat activatable expandable materials using an Intake/Rewet test. In the Intake/Rewet test, sample materials are cut into 3.5"×4" size, layered with treated side facing up on one layer of absorbent airlaid intake material (125 gsm absorbent airlaid from Glatfelter of Gatineau, Quebec, Canada) and covered with a second layer of airlaid absorbent material (240 gsm absorbent airlaid with 25% superabsorbent material (SAM) from Glatfelter of Gatineau, Quebec, Canada). A polyethylene film pouch was placed under the layered nonwovens. The top layer is then insulted with a first 2 ml gush of room temperature menses simulant (24 mL/min), followed by a 2 minute, 55 second pause, followed by a 3 ml trickle (0.3 mL/min), and then a second 2 ml gush (24 mL/min).

The $1^{st}$ and $2^{nd}$ Intake values are measured with a stopwatch during the first and second 2 ml gush respectively. The stopwatch is started when the gush starts and is stopped when the fluid from the gush is completely absorbed. Rewet values are determined after complete penetration of the second 2 ml gush. To measure rewet values, two pieces of blotting paper (Verigood grade, white, 300 g/m2, 48.26 by 60.96 cm stock, 250 sheets per ream, Georgia-Pacific Corporation part number 411-01-12, or equivalent) are placed to cover the insulted sample material along with the airlaid materials and PE film pouch. A foot that covers the sample is lowered against the blotter paper to create a pressure load of 1.0 psi for 3 minutes and the amount of fluid transferred to the blotting paper is determined gravimetrically. The pressure used in this test has been shown to correlate well with the pressures applied to feminine hygiene pads during use.

The menses simulant used in above tests is purchased from Cocalico Biologicals and is prepared according to U.S. Pat. No. 5,883,231. The final menses simulant formulation consists of 42% thick egg whites, 28% plasma, and 30% packed red blood cells.

Each sample was tested multiple times to obtain an average reading. The average was determined by individually calculating the intake and rewet values for each of the test specimens, summing the values, and then dividing by the number of samples to get the average value.

In the following examples, heat-activatable expandable treatments were applied to nonwoven fibrous webs by pattern roll coating in various patterns and allowed to dry.

The intake rates and rewet values of each sample were determined according to the test method explained above.

EXAMPLE 1

Figure 4:
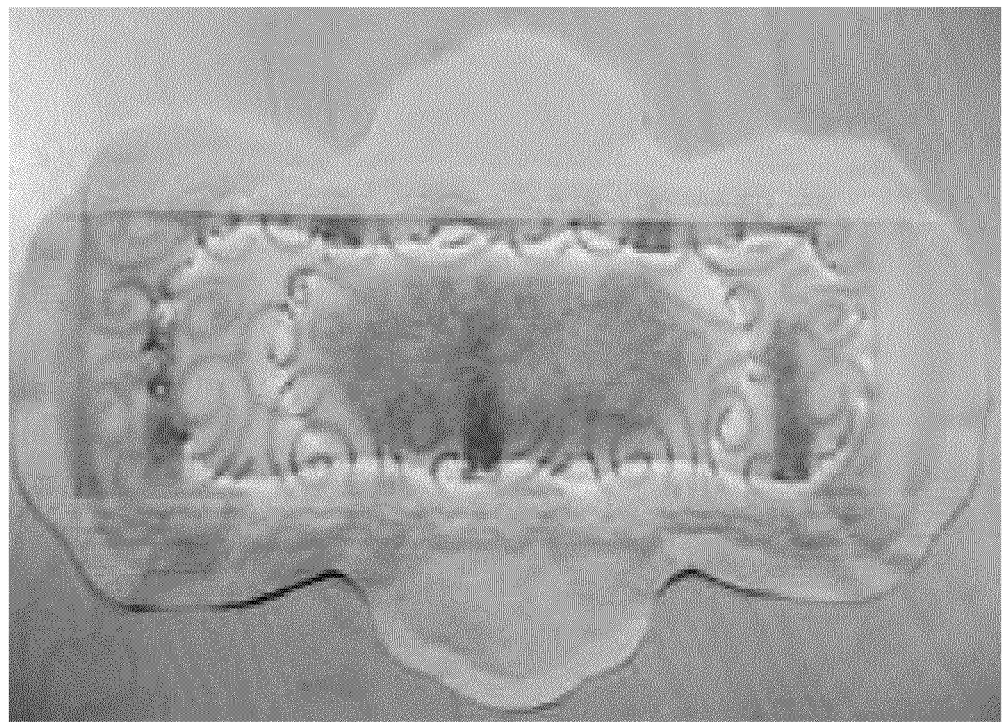
FIG. 4 depicts a pattern of heat activatable expandable ink as described in Example 1.

Light green color heat-activatable expandable ink (Puff Ink MW4319, available from Polytex Environmental Inks, Ltd) was applied to the underside of a body-side liner through air bonded carded web (available from Dayuan) in a pattern as shown in FIG. 4. The treated through air bonded carded web (TABCW) showed greatly improved rewet bench test results—reduced from 1.14 g to 0.77 g when using the rewet test described above. Both $1^{st}$ and $2^{nd}$ Intake results showed improvement (faster intake) for the treated TABCW samples.

|  | 1st Intake (sec) | 2nd Intake (sec) | Rewet (g) |
| --- | --- | --- | --- |
| TABCW (from Dayuan) | 9.0 | 20.6 | 1.14 |
| Puff Ink Coated TABCW (from Dayuan) | 8.5 | 16.4 | 0.77 |

EXAMPLE 2

Figure 5:
FIG. 5 depicts a pattern of heat activatable expandable ink as described in Example 2.

Light blue color heat-activatable expandable ink (Puff Ink MW 4404 available from Polytex Environmental Inks, Ltd) was applied to the upper side of a through air bonded carded web (available from Sambo) surge layer in a pattern as shown in FIG. 5 where the surge layer is under a TABCW body side liner material. The treated TABCW showed greatly improved rewet bench test results—reduced from 1.16 g to 0.68 g when using the rewet test as described above. The $2^{nd}$ Intake result showed improvement as well for the treated TABCW samples.

|  | $1^{st}$ Intake (sec) | $2^{nd}$ Intake (sec) | Rewet (g) |
| --- | --- | --- | --- |
| TABCW (from Sambo) | 8.0 | 20.4 | 1.16 |

| | 1st Intake (sec) | 2nd Intake (sec) | Rewet (g) |
|---|---|---|---|
| Puff Ink Coated TABCW (from Sambo) | 8.9 | 15 | 0.68 |

EXAMPLE 3

Figure 6:
FIG. 6 depicts a pattern of heat activatable expandable ink as described in Example 3.

Light blue color heat-activatable expandable ink (Puff Ink MW 4404 available from Polytex Environmental Inks, Ltd) was applied to the upper side of a Spunlace surge layer material in a pattern as shown in FIG. 6 where the surge layer is under a spunbonded body side liner material. The treated Spunlace showed greatly improved rewet bench test results—reduced from 1.19 g to 0.86 g when using the rewet test described above. The $2^{nd}$ Intake result showed improvement as well for the treated Spunlace samples.

| | 1st Intake (sec) | 2nd Intake (sec) | Rewet (g) |
|---|---|---|---|
| Spunlace | 9.3 | 25.8 | 1.19 |
| Puff Ink Coated Spunlace | 17.4 | 18.5 | 0.86 |

As shown, the addition of the heat-activatable expandable treatment to the nonwovens can increase the intake rate and decrease the rewet.

Although only a few exemplary embodiments of this invention have been described in detail above, those skilled in the art will readily appreciate that many modifications are possible without materially departing from the novel teachings and advantages of this invention. For example, features described in relation to one embodiment may be incorporated into any other embodiment of the invention.

Accordingly, all such modifications are intended to be included within the scope of this invention, which is defined in the following claims and all equivalents thereto. Further, it is recognized that many embodiments may be conceived that do not achieve all of the advantages of some embodiments, particularly of the desirable embodiments, yet the absence of a particular advantage shall not be construed to necessarily mean that such an embodiment is outside the scope of the present invention. As various changes could be made in the above constructions without departing from the scope of the invention, it is intended that all matter contained in the above description shall be interpreted as illustrative and not in a limiting sense.

What is claimed is:

1. An absorbent article having a longitudinal direction, a transverse direction, a longitudinally-extending centerline, a transverse-extending centerline, first and second longitudinally opposed end portions, and first and second side edges, the absorbent article comprising:
   a. a first major surface which forms a body-facing surface of the absorbent article;
   b. a second major surface disposed distally from the first major surface which forms a garment-facing surface of the absorbent article;
   c. an absorbent core positioned between the first major surface and the second major surface; and
   d. at least one heat-activatable expandable structure;
      wherein the heat-activatable expandable structure is on a nonwoven material and the heat-activatable expandable structure comprises from about 0.5 weight percent to about 10 weight percent of the weight of the nonwoven material.

2. The absorbent article of claim 1 wherein the at least one heat-activatable expandable structure is positioned between the first major surface and the absorbent core.

3. The absorbent article of claim 2 wherein the at least one heat-activatable expandable structure defines a channel between the first major surface and the absorbent core.

4. The absorbent article of claim 1 wherein the at least one heat-activatable expandable structure is positioned on the first major surface.

5. The absorbent article of claim 1 wherein the at least one heat-activatable expandable structure has a thickness above the first major surface of greater than about 0.1 millimeter.

6. The absorbent article of claim 1 wherein the at least one heat-activatable expandable structure comprises a heat-activatable expandable ink.

7. The absorbent article of claim 1 wherein the heat-activatable expandable structure comprises a moisture absorbing polymer.

8. The absorbent article of claim 1 wherein the heat-activatable expandable structure comprises an elastomeric polymer.

9. The absorbent article of claim 1 wherein the at least one heat-activatable expandable structure extends around the periphery of the first major surface to form a closed shape.

10. The absorbent article of claim 1 wherein the at least one heat-activatable expandable structure is positioned around a target zone of the absorbent article.

11. The absorbent article of claim 1 wherein the at least one heat-activatable expandable structure extends along one of the side edges.

12. The absorbent article of claim 1 wherein the at least one heat-activatable expandable structure extends along one of the end portions.

13. The absorbent article of claim 1 further comprising side panels for attaching the absorbent article to an undergarment.

14. The absorbent article of claim 1 further comprising a garment fastening system for attaching the absorbent article to an undergarment.

15. The absorbent article of claim 1 further comprising at least one of an intake layer, a cover, and/or a backsheet.

16. The absorbent article of claim 1 wherein the absorbent article is a feminine care pad.

17. The absorbent article of claim 1 wherein the nonwoven material with the heat-activatable expandable structure has rewet value less than about 1.1.

18. The absorbent article of claim 1 wherein the nonwoven material with the heat-activatable expandable structure has a rewet value less than about 1.0.

19. The absorbent article of claim 1 wherein the nonwoven material with the heat-activatable expandable structure has a rewet value between about 0.6 and about 1.1.

* * * * *